(12) United States Patent
Schwab et al.

(10) Patent No.: US 11,517,515 B2
(45) Date of Patent: Dec. 6, 2022

(54) HYBRID QUATS IN, IN PARTICULAR, HAIR TREATMENT AGENTS

(71) Applicant: Evonik Operations GmbH, Essen (DE)

(72) Inventors: Peter Schwab, Essen (DE); Stefan Neubauer, Cologne (DE); Patrick Winter, Mülheim an der Ruhr (DE)

(73) Assignee: Evonik Operations GmbH, Essen (DE)

( * ) Notice: Subject to any disclaimer, the term of this patent is extended or adjusted under 35 U.S.C. 154(b) by 232 days.

(21) Appl. No.: 16/973,560

(22) PCT Filed: Jun. 26, 2019

(86) PCT No.: PCT/EP2019/066928
§ 371 (c)(1),
(2) Date: Dec. 9, 2020

(87) PCT Pub. No.: WO2020/007670
PCT Pub. Date: Jan. 9, 2020

(65) Prior Publication Data
US 2021/0251865 A1 Aug. 19, 2021

(30) Foreign Application Priority Data
Jul. 5, 2018 (EP) .................................... 18181832

(51) Int. Cl.
*A61Q 5/12* (2006.01)
*A61K 8/41* (2006.01)
*A61K 8/34* (2006.01)

(52) U.S. Cl.
CPC .............. *A61K 8/416* (2013.01); *A61K 8/342* (2013.01); *A61Q 5/12* (2013.01); *A61K 2800/48* (2013.01)

(58) Field of Classification Search
None
See application file for complete search history.

(56) References Cited

U.S. PATENT DOCUMENTS

| | | | |
|---|---|---|---|
| 4,339,391 A | 7/1982 | Hoffmann et al. | |
| 4,874,554 A | 10/1989 | Lange et al. | |
| 5,609,167 A | 3/1997 | Hensen et al. | |
| 7,074,419 B2 | 7/2006 | Dietz et al. | |
| 7,731,982 B2 | 6/2010 | Schroder | |
| 8,211,972 B2 | 7/2012 | Meyer et al. | |
| 8,466,248 B2 | 6/2013 | Meyer et al. | |
| 9,073,818 B2 | 7/2015 | Herrwerth et al. | |
| 9,801,797 B2 | 10/2017 | Koehle et al. | |
| 2007/0081965 A1 | 4/2007 | Daou et al. | |
| 2011/0237667 A1 | 9/2011 | Loeffler et al. | |
| 2013/0071343 A1 | 3/2013 | Herrwerth et al. | |
| 2018/0228718 A1 | 8/2018 | Nguyen et al. | |
| 2019/0021968 A1* | 1/2019 | von Aspern ............. A61K 8/37 |

FOREIGN PATENT DOCUMENTS

| | | |
|---|---|---|
| DE | 2928603 | 2/1981 |
| DE | 3623215 | 1/1988 |
| DE | 4138630 A1 | 5/1993 |
| DE | 10 2008 015 899 A1 | 10/2008 |
| DE | 10 2008 001 788 | 11/2009 |
| DE | 10 2010 029 606 A1 | 12/2011 |
| DE | 10 2010 029 610 A1 | 12/2011 |
| EP | 1 125 574 A2 | 8/2001 |
| EP | 2 168 564 A2 | 3/2010 |
| EP | 2 198 827 A2 | 6/2010 |
| EP | 2 783 677 A2 | 10/2014 |
| FR | 2862210 A1 | 5/2005 |
| WO | 2004/112731 A2 | 12/2004 |
| WO | 2006/034992 A1 | 4/2006 |
| WO | 2008/092676 A1 | 8/2008 |
| WO | 2009/138306 A1 | 11/2009 |
| WO | 2017/021444 A1 | 2/2017 |

OTHER PUBLICATIONS

EP Search Report dated Jan. 7, 2019 in EP 18181832.9 (10 pages).
English translation of International Search Report dated Aug. 8, 2019 in PCT/EP2019/066928 (4 pages).
German language International Search Report dated Aug. 8, 2019 in PCT/EP2019/066928 (5 pages).

* cited by examiner

*Primary Examiner* — Jyothsna A Venkat
(74) *Attorney, Agent, or Firm* — Taylor English Duma LLP; Philip P. McCann

(57) ABSTRACT

The invention relates to compositions comprising
A) at least one hybrid quat and
B) at least one fatty alcohol.

11 Claims, 1 Drawing Sheet

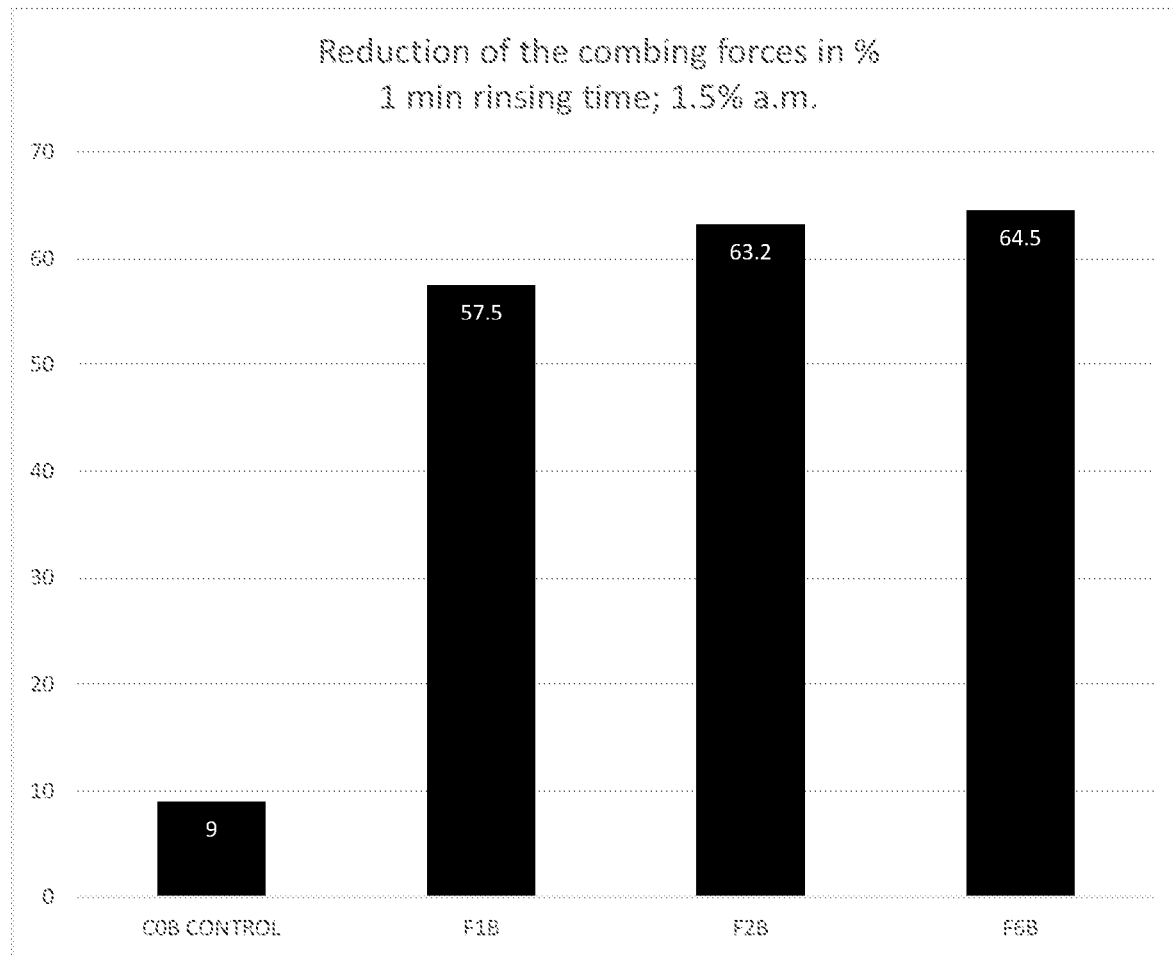
Combing force measurements

HYBRID QUATS IN, IN PARTICULAR, HAIR TREATMENT AGENTS

CROSS REFERENCE TO RELATED APPLICATIONS

This application is a 35 U.S.C. § 371 U.S. national phase entry of International Application No. PCT/US2019/066928 having an international filing date of Jun. 26, 2019, which claims the benefit of European Application No. 18181832.9 filed Jul. 5, 2018, both of which are incorporated herein by reference in its entirety.

FIELD

The invention relates to compositions comprising
A) at least one hybrid quat and
B) at least one fatty alcohol.

BACKGROUND

Alkyl quats and ester quats are used in cosmetic formulations as hair conditioning agents. Both have certain disadvantages: alkyl quats, especially dialkyl quats, are generally poorly biodegradable and contaminate the environment. Ester quats, especially TEA ester quats, are sensitive to hydrolysis and therefore can only be used in aqueous formulations to a limited extent.

It could now be shown that alkyl ester quats (hybrid quats), consisting of an ammonium salt having at least one fatty alkyl chain and at least one ester group esterified with fatty acid, have excellent conditioning properties and at the same time do not have the disadvantages of the alkyl quats or ester quats.

Surprisingly, it has also been found in addition that the alkyl ester quats are capable of creating exceptionally high viscosities in formulations with fatty alcohol.

DE3623215 discloses cosmetic hair compositions comprising highly ethoxylated hybrid quats and fatty alcohol.

DE2928603 discloses hybrid quats and use thereof as laundry fabric softeners.

The object of the invention was to provide alternative hair conditioning agents based on quaternized ammonium compounds.

SUMMARY

It has been found that, surprisingly, the hybrid quats described below are able to solve the problem addressed by the invention.

The present invention therefore relates to compositions comprising certain hybrid quats and fatty alcohol.

BRIEF DESCRIPTION OF THE DRAWINGS

FIG. 1 shows combing force measurements.

DETAILED DESCRIPTION

The invention further relates to the use of the particular hybrid quats for conditioning skin and keratin fibers, especially hair.

The invention further relates to the use of the hybrid quats for increasing the viscosity of fatty alcohol-containing compositions.

The present invention still further relates to the use of the hybrid quats as emulsifier, in particular a cationic emulsifier, in preferred cosmetic formulations.

An advantage of the present invention is that the composition according to the invention can be provided predominantly on the basis of natural raw materials.

A further advantage is that the hybrid quats used have improved stability to hydrolysis.

A further advantage is that the hybrid quats used have improved thermal stability.

A further advantage of the present invention is that good conditioning performance can be achieved without a negative influence on the formulation viscosity.

A further advantage is that the hybrid quats used can be processed extremely well. They can be used in particular in numerous different formulations.

A further advantage is that the hybrid quats used, in comparison to alkyl quats and ester quats, significantly increase the viscosities of fatty alcohol-based suspensions, as are typically used in conditioner rinse formulations. Therefore, the fatty alcohol content can be reduced which reduces the overall costs of the formulation.

A further advantage is that the hybrid quats used adequately stabilize the suspensions based on fatty alcohol even without a further emulsifier.

A further advantage is that the hybrid quats used can also be used in shampoos and thereby have a conditioning action.

A further advantage is that the hybrid quats used have good biodegradability.

A further advantage of the present invention is that the shine of the treated keratin fibers is increased.

A further advantage of the present invention is that the hybrid quats used develop a good effect even when used in small amounts.

A further advantage is that the hybrid quats used have little impact from an ecological point of view.

A further advantage is that the hybrid quats used exhibit an easier ability to be washed out on keratin fibers than quaternary ester compounds known hitherto.

A further advantage of the present invention is that the hybrid quats used do not crystallize out.

A further advantage of the present invention is that it protects hair colorant from washing out.

A further advantage of the present invention is that the hybrid quats can be formulated more easily.

A further advantage of the present invention is that the hybrid quats reduce combing forces on wet and dry hair.

A further advantage is that the hybrid quats used can be used in high active substance contents.

A further advantage of the present invention is that the hybrid quats used produce, as emulsifiers in O/W emulsions, an exceptional skin feel.

A further advantage of the present invention is that it is particularly economical.

A further advantage of the present invention is that the formulations with the hybrid quats have antistatic properties.

The present invention relates to compositions comprising
A) at least one hybrid quat of the general formula I)

general formula I)

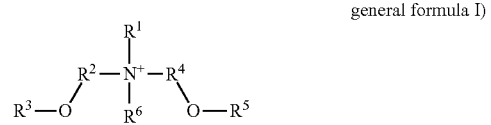

where
- $R^1$ is a hydrocarbon radical having 10 to 32 carbon atoms, preferably 12 to 22 carbon atoms, especially 16 to 18 carbon atoms
- $R^2$ and $R^4$ are each independently identical or different, selected from the group of divalent hydrocarbon radicals having 1 to 4 carbon atoms, especially $C_2H_4$ and $C_3H_6$,
- $R^3$ is an acyl radical of a fatty acid having a chain length of 8 to 32 carbon atoms, preferably 12 to 22 carbon atoms, particularly 16 to 22 carbon atoms, particularly preferably 16 to 18 carbon atoms,
- $R^5$ is H or an acyl radical of a fatty acid having a chain length of 8 to 32 carbon atoms, preferably 12 to 22 carbon atoms, particularly 16 to 22 carbon atoms, particularly preferably 16 to 18 carbon atoms,
- $R^6$ is selected from the group consisting of hydrocarbon radicals having 1 to 4 carbon atoms, especially ethyl and methyl,
B) at least one fatty alcohol.

The compositions according to the invention are preferably aqueous compositions.

In connection with the present invention, the term "aqueous" is to be understood as meaning a composition which comprises at least 5% by weight, preferably at least 30% by weight, in particular at least 70% by weight, of water, based on the total composition under consideration.

In connection with the present invention, the "pH" is defined as the value which is measured for the corresponding substance at 25° C. after stirring for five minutes using a pH electrode calibrated in accordance with ISO 4319 (1977).

In connection with the present invention, a "fatty alcohol" preferably has 8 to 32 carbons.

Unless stated otherwise, all percentages (%) given are percentages by mass.

Compositions preferred according to the invention are characterized in that
- A) is present in an amount of from 0.1% by weight to 10% by weight, preferably from 0.3% by weight to 5% by weight, in particular from 0.5% by weight to 3% by weight, and
- B) is present in an amount of from 1% by weight to 10% by weight, preferably from 2% by weight to 8% by weight, in particular from 3% by weight to 6% by weight, where the percentages by weight refer to the total composition.

It is preferred in accordance with the invention that in the at least one hybrid quat of the general formula I)
- $R^1$ is a hydrocarbon radical of a fatty alcohol.

In the context of the present invention, the term "hydrocarbon radical of a fatty alcohol" is the structure remaining after deletion of the OH group of the fatty alcohol.

Preferred radicals $R^1$ are hydrocarbon radicals of an unbranched or branched monoalcohol having an alkyl group of 10 to 30 carbon atoms, which may also be unsaturated. Preferred radicals $R^1$ are hydrocarbon radicals of decanol, lauryl alcohol, isolauryl alcohol, anteisolauryl alcohol, myristyl alcohol, isomyristyl alcohol, cetyl alcohol, palmoleyl alcohol, stearyl alcohol, isostearyl alcohol, anteisostearyl alcohol, eicosanol, petroselinyl alcohol, Guerbet alcohol, arachyl alcohol, gadoleyl alcohol, behenyl alcohol, erucyl alcohol, hectacosanol, octacosanol, and melissyl alcohol, and mixtures thereof, especially of technical-grade mixtures, preferably of technical-grade coconut fatty alcohols or tallow fatty alcohols having 12 to 18, preferably having 16 to 18 carbon atoms, and also of the monounsaturated fatty alcohols such as oleyl alcohol, elaidyl alcohol, delta-9-cis-hexadecenol, delta-9-octadecenol, trans-delta-9-octadecenol, cis-delta-11-octadecenol, trans-10,cis-12-hexadecadien-1-ol, octacosa-10,19-dien-1-ol and of polyunsaturated fatty alcohols such as, e.g. linoleyl alcohol (9Z, 12Z-octadecadien-1-ol), elaidolinoleyl alcohol (9E, 12E-octadecadien-1-ol), linolenyl alcohol (9Z, 12Z, 15Z-octadecatrien-1-ol), elaidolinolenyl alcohol (9E, 12E, 15-E-octadecatrien-1-ol), wherein particular preference is given to hydrocarbon radicals of mixtures of coconut fatty alcohols or tallow fatty alcohols having 16 to 18 carbon atoms.

$R^1$ is preferably the hydrocarbon radical of a fatty alcohol $R^1$—OH, which has a melting point greater than 25° C., particularly preferably greater than 50° C., at a pressure of 1 bar.

It is preferred in accordance with the invention that in the at least one hybrid quat of the general formula I)
- $R^1$ is a linear alkyl radical having 16 to 18 carbon atoms,
- $R^2$ and $R^4$ are each independently, identical or different, selected from the group comprising $C_2H_4$ and $C_3H_6$,
- $R^3$ is an acyl radical of a fatty acid having a chain length of 16 to 22, in particular 16 to 18, carbon atoms,
- $R^5$ is H or an acyl radical of a fatty acid having a chain length of 16 to 22, in particular 16 to 18, carbon atoms,
- $R^6$ is selected from the group consisting of ethyl and methyl.

The compositions according to the invention comprise at least one fatty alcohol (component B). Fatty alcohol in this context is preferably understood as meaning an unbranched or branched monoalcohol with an alkyl group of 8 to 30 carbon atoms, which may also be unsaturated. Preferred fatty alcohols are octanol, decanol, lauryl alcohol, isolauryl alcohol, anteisolauryl alcohol, myristyl alcohol, isomyristyl alcohol, cetyl alcohol, palmoleyl alcohol, stearyl alcohol, isostearyl alcohol, anteisostearyl alcohol, eicosanol, petroselinyl alcohol, Guerbet alcohol, arachyl alcohol, gadoleyl alcohol, behenyl alcohol, erucyl alcohol, hectacosanol, octacosanol, and melissyl alcohol, and mixtures thereof, in particular technical-grade mixtures, preferably technical-grade coconut or tallow fatty alcohols having 12 to 18, preferably having 16 to 18, carbon atoms, and also the monounsaturated fatty alcohols, such as oleyl alcohol, elaidyl alcohol, delta-9-cis-hexadecenol, delta-9-octadecenol, trans-delta-9-octadecenol, cis-delta-11-octadecenol, trans-10,cis-12-hexadecadien-1-ol, octacosa-10,19-dien-1-ol and polyunsaturated fatty alcohols such as e.g. linoleyl alcohol (9Z,12Z-octadecadien-1-ol), elaidolinoleyl alcohol (9E,12E-octadecadien-1-ol), linolenyl alcohol (9Z,12Z,15Z-octadecatrien-1-ol), elaidolinolenyl alcohol (9E,12E,15E-octadecatrien-1-ol), where mixtures of coconut or tallow fatty alcohols having 16 to 18 carbon atoms are particularly preferred.

Preference is given to a fatty alcohol which has a melting point greater than 25° C., particularly preferably greater than 50° C., at a pressure of 1 bar.

The fatty alcohol is preferably present in an amount of from 0.5 to 20% by weight, preferably 1 to 10% by weight, in particular 2 to 7% by weight, in the composition according to the invention, where the percentages by weight refer to the total composition.

It has proven to be advantageous if the compositions according to the invention additionally comprise a component C) emulsifier, in particular in an amount of from 0.1 to 10% by weight, preferably 0.25 to 5% by weight, in particular 0.5 to 2.0% by weight, where the percentages by weight refer to the total composition.

Preferably present emulsifiers are nonionic emulsifiers.

Emulsifiers preferred in this context are selected from the group of the fatty alcohol alkoxylates, in particular the fatty alcohol ethoxylates. Particularly preferred fatty alcohol ethoxylates present are selected from the group comprising polyoxyethylene ethers of lauryl alcohol, CAS number 9002-92-0, macrogol lauryl ether, e.g. polyoxyethylene (4) lauryl ether (Laureth-4, INCI), polyoxyethylene (9) lauryl ether Laureth-9 (INCI),
polyoxyethylene (23) lauryl ether Laureth-23 (INCI)
polyoxyethylene ethers of cetyl alcohol, CAS number 9004-95-9, e.g.
polyoxyethylene (2) cetyl ether Ceteth-2 (INCI)
polyoxyethylene (10) cetyl ether Ceteth-10 (INCI)
polyoxyethylene (20) cetyl ether Ceteth-20 (INCI)
polyoxyethylene ethers of cetylstearyl alcohol, CAS number 68439-49-6, e.g.
polyoxyethylene (6) cetylstearyl ether Ceteareth-6 (INCI)
polyoxyethylene (20) cetylstearyl ether Ceteareth-20 (INCI)
polyoxyethylene (25) cetylstearyl ether Ceteareth-25 (INCI)
polyoxyethylene ethers of stearyl alcohol, CAS number 9005-00-9, e.g.
polyoxyethylene (2) stearyl ether Steareth-2 (INCI)
polyoxyethylene (10) stearyl ether Steareth-10 (INCI)
polyoxyethylene (20) stearyl ether Steareth-20 (INCI)
polyoxyethylene ethers of oleyl alcohol, CAS number 9004-98-2, e.g.
polyoxyethylene (2) oleyl ether Oleth-2 (INCI)
polyoxyethylene (10) oleyl ether Oleth-10 (INCI)
polyoxyethylene (20) oleyl ether Oleth-20 (INCI) or
polyoxyethylene (10) tridecyl ether (CAS number 24938-91-8) and Trideceth-10 (INCI).

Alternatively preferred emulsifiers are selected from the group of polyol esters, in particular the glycerol esters and polyglycerol esters, in particular the polyglycerol esters. Preferably present (poly)glycerol esters are characterized in that they are partial esters. Particularly preferred polyglycerol partial esters are selected from the group comprising polyglycerol partial esters as described in EP-B-0 835 862, which are obtainable by esterification of a polyglycerol mixture with a degree of esterification of the polyglycerol between 30 and 75% and saturated or unsaturated, linear or branched fatty acids with 12 to 22 carbon atoms and dimer fatty acids with an average functionality of 2 to 2.4, esters of citric acid such as, for example, the O/W emulsifier glyceryl stearate citrate, (2-hydroxy-1,2,3-propanetricarboxylic acid-1,2,3-propanetriol monooctadecanoate, INCI Glyceryl Stearate Citrate, CAS 39175-72-9), the citric acid ester of glyceryl stearate, commercially available inter alia under the name AXOL C 62, glyceryl stearate citrate as described in WO2006034992 and WO2008092676 and glyceryl oleate citrate as described in WO2004112731, likewise simple polyglycerol esters, such as, for example, polyglycerol-3 distearate, polyglyceryl-10 stearate, polyglyceryl-6 distearate, mixed esters of polyglycerol and methylglucose and stearic acid, such as, for example, polyglyceryl-3 methyl glucose distearate and (poly)glycerol partial esters with one or more carboxylic acids having 10 to 24 carbon atoms and residues of a polyfunctional carboxylic acid.

In principle, sorbitan or sucrose esters can also be used as polyol esters. A customary combination is, for example, Sorbitan Stearate & Sucrose Cocoate.

Emulsifiers preferably present in a further alternative are selected from the group of modified siloxanes, for example those which also bear polyethers besides aliphatic groups based on alpha-olefins. Siloxane-based emulsifiers for oil-in-water emulsions must have a hydrophilic character, for which reason they are generally pure polyether siloxanes. Particularly suitable examples are relatively hydrophobic polyethersiloxanes as described in EP 1125574, high molecular weight polyethersiloxanes as described in EP2168564 and organomodified siloxane block copolymers as described in WO2009138306. Preferably present modified siloxanes are characterized in that they have an HLB value >8. Particularly preferred modified siloxanes are selected from the group comprising Bis-PEG/PPG-16/16 Dimethicone, PEG/PPG-16/16 Dimethicone, Bis-PEG/PPG-20/5 PEG/PPG-20/5 Dimethicone and Methoxy PEG/PPG-25/4 Dimethicone. In connection with the present invention, the aforementioned emulsifiers produce particularly storage-stable formulations.

Preferred compositions according to the invention are emulsions, preferably oil-in-water emulsions, particularly preferably emulsions in which the oil phase is solid at 25° C., an oil-in-water suspension thus being present at 25° C.

The compositions according to the invention advantageously have, at 25° C., a pH of from 1 to 6.9, particularly preferably from 2 to 6.5, in particular from 2.5 to 6.

It has proven to be advantageous if the compositions according to the invention additionally comprise a component D) surfactant, in particular in an amount of from 0.1 to 10% by weight, preferably 0.25 to 5% by weight, in particular 0.5 to 2.0% by weight, where the percentages by weight refer to the total composition.

In the context of the present invention, the term "surfactant" is understood to mean organic substances with interface-active properties which have the ability to reduce the surface tension of water at 20° C. and at a concentration of 0.5% by weight, based on the total composition, to below 45 mN/m. The surface tension is determined here by the ring method in accordance with du Noüy at 25° C.

The surfactants are in particular nonionic surfactants, anionic surfactants, cationic surfactants and amphoteric (zwitterionic) surfactants.

Preference is given to compositions according to the invention which are characterized in that the surfactant is selected from the group comprising, preferably consisting of:

anionic surfactants, cationic surfactants and amphoteric surfactants, with anionic surfactants and cationic surfactants being particularly preferred.

If the composition according to the invention comprises an anionic surfactant, preference is given in particular to compositions according to the invention which are characterized in that the anionic surfactant is selected from the group comprising, preferably consisting of:

alkyl sulfates in the form of their alkali metal, ammonium or alkanolammonium salts, alkyl ether sulfates,
alkyl phosphates in the form of their alkali metal, ammonium or alkanolammonium salts, alkyl ether carboxylates in the form of their alkali metal or ammonium salts, acyl sarcosinates in the form of their alkali metal or ammonium salts, sulfosuccinates in the form of their alkali metal or ammonium salts and acyl glutamates in the form of their alkali metal or ammonium salts, particular preference being given to alkyl sulfates and alkyl ether sulfates.

If the composition according to the invention comprises a cationic surfactant, preference is given in particular to compositions according to the invention which are characterized in that the cationic surfactant is selected from the group of the quaternary ammonium compounds, preferably consisting of alkyltrimethylammonium compounds, with palmitamidopropyltrimonium chloride being particularly preferred.

If the composition according to the invention comprises an amphoteric surfactant, preference is given in particular to compositions according to the invention which are characterized in that the amphoteric surfactant is selected from the group comprising, preferably consisting of:

betaines, amphoacetates and amphopropionates,

N-alkyl-N,N-dimethylammoniumglycinates, for example cocoalkyldimethylammonium glycinate, N-acylaminopropyl-N,N-dimethylammonium glycinates, for example cocoacylaminopropyldimethylammonium glycinate, 2-alkyl-3-carboxylmethyl-3-hydroxyethylimidazolines having in each case 8 to 18 carbon atoms in the alkyl or acyl group, and also cocoacylaminoethylhydroxyethylcarboxymethylglycinate, compounds which, apart from a C8/18-alkyl or-acyl group in the molecule, comprise at least one free amino group and at least one —COOH— or —SO$_3$H group and are capable of forming internal salts, such as, for example, N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids having in each case about 8 to 18 carbon atoms in the alkyl group, N-cocoalkylaminopropionate, cocoacylaminoethylaminopropionate and C12/18-acylsarcosine, with N-acylaminopropyl-N,N-dimethylammonium glycinates being particularly preferred.

The compositions according to the invention can comprise e.g. at least one further, additional component selected from the group of
emollients,
co-emulsifiers,
thickeners/viscosity regulators/stabilizers,
antioxidants,
hydrotropes (or polyols),
solids and fillers,
pearlescence additives,
deodorant and antiperspirant active ingredients,
insect repellents,
self-tanning agents,
preservatives,
conditioning agents,
perfumes,
dyes,
cosmetic active ingredients,
care additives,
superfatting agents,
solvents.

Substances which can be used as exemplary representatives of the individual groups are known to the person skilled in the art and can be found for example in the German application DE 102008001788.4. This patent application is herewith incorporated as reference and thus forms part of the disclosure.

As regards further optional components and the amounts used of these components, reference is made expressly to the relevant handbooks known to the person skilled in the art, e.g. K. Schrader, "Grundlagen and Rezepturen der Kosmetika [Fundamentals and formulations of cosmetics]", 2nd edition, pages 329 to 341, Hüthig Buch Verlag Heidelberg.

The amounts of the particular additives are guided by the intended use.

Typical guide formulations for the respective applications are known prior art and are contained for example in the brochures of the manufacturers of the particular basic materials and active ingredients. These existing formulations can generally be adopted unchanged. If necessary, the desired modifications can, however, be undertaken without complication by means of simple experiments for the purposes of adaptation and optimization.

The hybrid quats of the general formula I) present in the compositions according to the invention and also the compositions according to the invention can be used in accordance with the invention for the cosmetic treatment of skin or keratin fibers, particularly for hair treatment, particularly preferably for conditioning hair.

In this connection, preference is given to preferably using those hybrid quats of the general formula I) which are described above as preferably being present in the compositions according to the invention.

The use according to the invention leads to the improvement in the conditioning, shine, flexibility, elasticity and/or combability, and also to a reduction in the probability of breakage of the treated fibers and, moreover, it reduces the static forces between the fibers.

The present invention still further relates to the use of the hybrid quats of the general formula I) present in the compositions according to the invention for modifying the viscosity, especially thickening, of a composition comprising at least one fatty alcohol.

In this connection, preference is given to preferably using those hybrid quats of the general formula I) which are described above as preferably being present in the compositions according to the invention.

The present invention further relates to the use of the hybrid quats present in the compositions according to the invention as emulsifier, in particular cationic emulsifier, in preferably cosmetic formulations, in particular to give O/W emulsions.

In this connection, preference is given to preferably using those hybrid quats of the general formula I) which are described above as preferably being present in the compositions according to the invention.

The examples adduced hereinafter describe the present invention by way of example, without any intention that the invention, the scope of application of which is apparent from the entirety of the description and the claims, be restricted to the embodiments specified in the examples.

The following figures are part of the examples:
FIG. 1: Combing Force Measurements

EXAMPLES

TABLE A

Amines having two hydroxyethyl groups and fatty alcohol radicals $R^1$

| Amine | $R^1$ (all % figures are mol %) | $R^2$ | $R^4$ | Trade name | Source |
|---|---|---|---|---|---|
| A1 | Stearyl having 93% C18, 5% C16, 2% > C20 with IN = 0-3.0 | $C_2H_4$ | $C_2H_4$ | Varonic S 202 | Evonik Corporation, USA |
| A2 | Tallow having 3% C14, 30% C16, 67% C18 with IN = 38.0-54.0 | $C_2H_4$ | $C_2H_4$ | Varonic T 202 | Evonik Corporation, USA |
| A3 | Hydr. tallow having 3% C14, 30% C16, 67% C18 with IN <= 3.0 | $C_2H_4$ | $C_2H_4$ | Varonic U 202 | Evonik Corporation, USA |

TABLE B

Radicals $R^3$ or, if appropriate, fatty acid defining $R^5$

| Fatty acid | Source | Iodine number |
|---|---|---|
| FA1 | Coconut fatty acid, Wilfarin DC-0818, Wilmar | <12 |
| FA2 | Stearic fatty acid, plant-based, Pristeren 4928, Croda | <1.0 |
| FA3 | Mixed vegetable oil fatty acid, Nouracid IF 10, Oleon | 110-125 |
| FA4 | 12-Hydroxystearic acid, Alberdingk Boley | <5 |

Example E1 to E6

482.8 g (1.325 mol) of amine A1 were placed in a three-necked flask equipped with column, distillation system and stirrer motor and heated to 80° C. under a nitrogen atmosphere. To this were added 332.8 g (1.59 mol) of fatty acid FA 1 and 0.4 g of 50% aqueous hypophosphorous acid. A vacuum of 100 mbar was applied and the mixture was cautiously heated to 195° C., wherein water of reaction was collected in the outflow of the distillation system. After 3 hours, the vacuum was lowered to 20 mbar and further reacted for 2 hours. The condensation product thus obtained had an acid number of 1.3 mg KOH/g and an amine number of 94.0 mg KOH/g. The reaction mixture was cooled to 80° C. Over one hour, 155.4 g (1.232 mol) of dimethyl sulfate were added dropwise with stirring, wherein the temperature was maintained in a range of 80-95° C. Subsequently, 103 g of anhydrous ethanol were added and the mixture further stirred at 80° C. for one hour. The product thus obtained had an amine number of 3.0 mg KOH/g.

The further examples E2-E6 and comparative examples were carried out according to this procedure but with varied reactants or varied amount ratios—in each case as stated in table C below.

TABLE C

| Example | Amine | Fatty acid | Iodine number | Moles of fatty acid per mole of amine | Experiment number |
|---|---|---|---|---|---|
| E1 | A1 | FA1 | <12 | 1.2 | TS 324/16 |
| E2 | A1 | FA2 | <1.0 | 0.8 | AE 323//16 |
| E3 | A1 | FA3 | 110-125 | 0.8 | MK 320/16 |
| E4 | A1 | FA3 | 110-125 | 1.5 | TS 321/16 |
| E5 | A3 | FA2 | <1.0 | 1.5 | TS 13/17 |
| E6 | A2 | FA4 | <5 | 1.0 | TS 252/16 |

Example E9

89.8 g (0.445 mol) of lauric acid, 125.7 g (0.445 mol) of oleic acid and 209.5 g (0.897 mol) of behenic acid were initially charged at 70° C. To this, in a three-necked flask equipped with a distillation column attachment, were added dropwise 324.9 g (0.938 mol) of N,N-bis(2-hydroxyethyl)-N-octadecylamine and the mixture was heated slowly to 190° C. and the water of reaction was distilled off. After 2 hours a vacuum of 25 mbar was applied, which was later further reduced to 8 mbar. After 8 hours, an acid number of 3.5 mgKOH/g was reached. The reaction mixture was cooled to 60° C. 771.4 g of the diester thus obtained were mixed with 448 g of C16/C18 fatty alcohol. 101 g (0.80 mol) of dimethyl sulfate were added gradually to the reaction mass and reacted at 80-90° C. The product thus obtained had a total amine number of 2.9 mgKOH/g.

Active content: 0.50 meq/g; 34% fatty alcohol

Comparative Example CE10 in Accordance with DE10210029606

179.5 g (0.89 mol) of lauric acid, 251.4 g (0.89 mol) of oleic acid and 619 g (1.795 mol) of behenic acid were initially charged at 70° C. To this, in a three-necked flask equipped with a distillation column attachment, were added dropwise 223.50 g (1.875 mol) of methyldiethanolamine and the mixture was heated slowly to 190° C. and the water of reaction was distilled off. After 2 hours a vacuum of 25 mbar was applied, which was later further reduced to 8 mbar. After 8 hours, an acid number of 4.3 mgKOH/g was reached. The reaction mixture was cooled to 60° C. 783 g of the diester thus obtained were mixed with 448 g of C16/C18 fatty alcohol. 146 g (1.159 mol) of dimethyl sulfate were added gradually to the reaction mass and reacted at 90° C. The product thus obtained had a total amine number of 2.8 mgKOH/g.

Active content: 1.05 meq/g; 32.5% fatty alcohol

Comparative Example CE11

315.9 g (2.65 mol) of methyldiethanolamine, 666.7 g (3.18 mol) of coconut fatty acid (Wilfarin DC-0818, Wilmar) and 0.5 g of 50% hypophosphorus acid were carefully heated to 195° C. under a nitrogen atmosphere in a three-necked flask equipped with a distillation column attachment. The water of reaction was distilled off over 3 hours. A vacuum of 20 mbar was then applied and the mixture was reacted for a further 2 hours until an acid number of 1.6 mgKOH/g was reached. 199.7 g (1.583 mol) of dimethyl sulfate were added gradually to 576 g of the diester thus obtained and the mixture was stirred at 80-95° C. 86.2 g of anhydrous ethanol were then added and the mixture was stirred at 80° C. The product thus obtained had a total amine number of 3.0 mgKOH/g.

Active content: 1.5 meq/g; 10% ethanol, no fatty alcohol

Example 2

Application Technology of Hair Treatment Compositions Using Examples E1, E2 and E6 and Commercial Market Products For the applications-related assessment, hair tresses were used which had been predamaged in a standardized manner by means of a bleaching treatment. For this purpose, standard hairdressing products are used. The damage to the hair tresses is described in detail in DE10327871.

For the application-related assessment, the compounds according to the invention from Example E1, E2 and E6 were used in a simple cosmetic formulation.

The reference compounds used were the commercially available alkyl quat (INCI) Behentrimonium Chloride (VARISOFT® BT 85 Pellets, Evonik Nutrition & Care) and the commercially available ester quat (INCI) Distearoylethyl Hydroxyethylmonium Methosulfate (VARISOFT® EQ F 75, Evonik Nutrition & Care).

The application properties upon use in hair rinses were tested in the following formulations (Tab. 1 and 1b):

TABLE 1

Hair rinse formulations for testing the hair conditioning properties

| | C0a | F1a | F2a | F5a | F6a | V7a | V8a |
|---|---|---|---|---|---|---|---|
| TEGINACID® C, Evonik Industries (INCI: Ceteareth-25) | 0.5% | 0.5% | 0.5% | 0.5% | 0.5% | 0.5% | 0.5% |
| TEGO® Alkanol 1618, Evonik Nutrition & Care (INCI: Cetearyl Alcohol) | 5% | 5% | 5% | 5% | 5% | 4.67% | 5% |
| Example E1 (90%) | | 1.1% | | | | | |
| Example E2 (90%) | | | 1.1% | | | | |
| Example E5 (90%) | | | | 1.1% | | | |
| Example E6 (90%) | | | | | 1.1% | | |
| VARISOFT® EQ F 75, (75% in cetearyl alcohol), Evonik Nutrition & Care (INCI: Distearoylethyl Hydroxyethylmonium Methosulfate) | | | | | | 1.33% | |
| VARISOFT® BT 85, (85% in isopropanol), Evonik Nutrition & Care (INCI: Behentrimonium Chloride) | | | | | | | 1.17% |
| Water, demineralized | to 100.0 | to 100.0 | to 100.0 | to 100.0 | to 100.0 | to 100.0 | to 100.0 |
| Citric acid (to pH = 4) | | | | | | | |

TABLE 1b

Hair rinse formulations for testing the hair conditioning properties

| | Formulation example | | |
|---|---|---|---|
| | F9a | V10a | V11a |
| TEGINACID ® C, Evonik Industries (INCI: Ceteareth-25) | 0.5% | 0.5% | 0.5% |
| TEGO ® Alkanol 1618, Evonik Nutrition & Care (INCI: Cetearyl Alcohol) | 4.5% | 4.5% | 5% |
| Example E9 (68% in cetearyl alcohol) | 1.5% | | |
| Comparative example CE10 (66% in cetearyl alcohol) | | 1.5 | |
| Comparative example CE11 (90% in ethanol) | | | 1.1 |
| Water, demineralized | to 100.0 | to 100.0 | to 100.0 |
| Citric acid (to pH = 4) | | | |

The composition of the test formulations is deliberately chosen to be simple in order to avoid the test results being influenced by (normally present) formulation constituents. Besides the specified ingredients and/or instead of the specified ingredients, formulations according to the invention can also comprise further ingredients. In particular, the combination with further ingredients can lead to a synergistic improvement in the case of the described effects. The hair is pretreated with a shampoo formulation (Tab. 2), which contains no conditioner.

TABLE 2

Shampoo formulation for the pretreatment of the hair tresses.

| | |
|---|---|
| Texapon NSO ®, 28%, Cognis (INCI: Sodium Laureth Sulfate) | 42.9% |
| NaCl | 3% |
| Water, demineralized | to 100.0 |

Standardized treatment of predamaged hair tresses with conditioning samples:

The hair tresses predamaged as described above are washed with the shampoo formulation from Tab. 2.

Here, the hair tresses are wetted under running warm water. The excess water is gently squeezed out by hand, then the shampoo is applied and worked gently into the hair for 1 min (0.5 ml/2 g hair tress). The hair tress is rinsed for 30 s under running warm water. This procedure is repeated once more except that final rinsing is for 1 min.

Then, directly after washing, the hair tresses are conditioned with the hair rinse formulations from Tab. 1.

Here, the rinse is applied and gently worked into the hair (0.5 ml/2 g hair tress). After a residence time of 1 min, the hair is rinsed for a) 1 min or for b) 3 min.

Before the dry sensory assessment, the hair is dried for at least 12 h in the air at 50% humidity and 25° C.

Assessment Criteria:

The sensory evaluations are made using grades awarded on a scale from 1 to 5, with 1 being the worst evaluation and 5 being the best evaluation. The individual test criteria each receive their own evaluation.

The test criteria are as follows:

Wet combability, wet feel, dry combability, dry feel.

In the following tables, the results of the sensory assessment of the treatment of the hair tresses, carried out as described above, in the case of a) 1 min rinsing time and in the case of b) 3 min rinsing time, are compared for the inventive formulations F1a, F2a, F6a, the comparative formulations V7a, V8a and the control formulation C0a (control without test substance).

a) 1 Min Rinsing Time

TABLE 3a

Results of the conditioning of hair at 1 min rinsing time

| | Wet combability | Wet feel | Dry combability | Dry feel |
|---|---|---|---|---|
| Inventive formulation F1a | 4.5 | 4.5 | 5 | 5 |
| Inventive formulation F2a | 4 | 4 | 5 | 5 |
| Inventive formulation F3a | 4 | 4 | 5 | 5 |
| Inventive formulation F9a | 4 | 4.5 | 4.5 | 4.5 |
| Comparative formulation V7a (F 75) | 3.5 | 3.5 | 3.5 | 3 |
| Comparative formulation V8a (BT 85) | 4 | 4 | 4 | 4 |
| Comparative formulation V10a (F 75) | 4 | 4 | 4 | 4 |
| Comparative formulation V11a (F 75) | 3 | 3 | 3.5 | 3.5 |
| Control C0a | 2 | 2 | 3 | 2.5 | b) 3 Min Rinsing Time

TABLE 3b

Results of the conditioning of hair at 3 min rinsing time

| | Wet combability | Wet feel | Dry combability | Dry feel |
|---|---|---|---|---|
| Inventive formulation F1a | 4 | 4 | 5 | 5 |
| Inventive formulation F2a | 4 | 4 | 4.5 | 5 |
| Inventive formulation F3a | 4 | 4 | 5 | 5 |
| Comparative formulation V7a (F 75) | 3 | 3 | 3 | 3 |
| Inventive formulation F9a | 4 | 4 | 4 | 4.5 |
| Comparative formulation V8a (BT 85) | 4 | 4 | 4 | 4 |
| Comparative formulation V10a | 3 | 3 | 3.5 | 3.5 |
| Comparative formulation V11a | 2 | 2.5 | 3 | 3 |
| Control C0a | 1.5 | 2 | 2.5 | 2 |

From the results in table 3a, the inventive formulations F1a, F2a, and F6a, in each case compared with the formulations V7a and V8a, show better performance, both with respect to combability and feel in the case of wet and dry hair. Particularly in the case of dry hair, the absolute values of the hybrid quats are excellent. Surprisingly, the hybrid quats at 3 minutes rinsing time show hardly any deterioration in the results. Particularly on the dry hair, the conditioning performance remains very high. All inventive formulations are classified as significantly better compared to the comparative formulations.

Example 3

Influence of the Inventive Compounds on Combing Forces of Hair

Experimental Conditions:
Instrument: Diastron MTT 175
Measurement distance: 20 cm
Combing rate: 2000 mm/min into the hair for 30 sec and then left on for 5 min, then rinsed off under running tap water for 1 min or 3 min.

To carry out the combing force measurement after treatment with the test formulation, points 3-5 are repeated.

The combability (%) is then calculated before and after treatment with the test formulation.

Test Formulations Used:

The combing forces when used in hair rinses were tested in the following formulations (Tab. 4):

TABLE 4

Hair rinse formulations for testing the combing forces and the antistatic properties

| | Formulation examples | | | | | | | | |
|---|---|---|---|---|---|---|---|---|---|
| | C0b | F1b | F2b | F6b | F9b | V7b | V8b | V10b | V11b |
| TEGINACID ® C, Evonik Industries (INCI: Ceteareth-25) | 0.5% | 0.5% | 0.5% | 0.5% | 0.5% | 0.5% | 0.5% | 0.5% | 0.5% |
| TEGO ® Alkanol 1618, Evonik Nutrition & Care (INCI: Cetearyl Alcohol) | 5% | 5% | 5% | 5% | 4.25% | 4.5% | 5% | 4.25% | 5% |
| Example E1 (90%) | | 1.65% | | | | | | | |
| Example E2 (90%) | | | 1.65% | | | | | | |
| Example E6 (90%) | | | | 1.65% | | | | | |
| Example E9 (68% in cetearly alcohol | | | | | 2.25% | | | | |
| VARISOFT ® EQ F 75, (75% in cetearyl alcohol), Evonik Nutrition & Care (INCI: Distearoylethyl Hydroxyethylmonium Methosulfate) | | | | | | 2% | | | |
| VARISOFT ® BT 85, (85% in isopropanol), Evonik Nutrition & Care (INCI: Behentrimonium Chloride) | | | | | | | 1.75% | | |
| Comparative example CE10 (66% in cetearyl alcohol) | | | | | | | | 2.25 | |
| Comparative example CE11 (90% in ethanol) | | | | | | | | | 1.65 |
| Water, demineralized | 100.0 | 100.0 | 100.0 | 100.0 | 100.0 | 100.0 | 100.0 | 100.0 | |
| Citric acid (to pH = 4) | | | | | | | | | |

Hair tresses used: length=23 cm; width=1.5 cm; weight=2 g Measurement conditions: T=22° C.

The hair tresses are measured with a residual moisture of 60%, determined by weight determination.

European, undamaged, dark brown hair is used for the experiments. To carry out the combing force measurements, this hair is damaged by means of perming in the laboratory in accordance with standard conditions:

1.) 4 g of perming solution/g of hair, leave to act for 15 min, rinse out for 2 min under running tap water (T=35° C.). (Perming solution: Universal perming, Basler) 2.) 4 g of neutralizer (1 part neutralizing solution+3 parts water)/g of hair, allow to act for 10 min, rinse out for 2 min. (Neutralizing solution: foam neutralizer concentrate, Basler)

Carrying out the combing force measurement before the treatment with the test formulation:

The predamaged hair tresses are climatized overnight.

3.) The hair tress is dipped for 1 min in a buffer solution (Na citrate, pH=6). 4.) The hair tress is precombed by hand until no change in combing resistance can be ascertained. 5.) The hair tress is clamped in the instrument and the first combing force measurement is carried out. The measurement is repeated a total of 10 times.

Treatment of the Tresses:

0.5 g of the respective test formulation is used per hair tress (2 g hair/0.5 g solution). The formulation is massaged FIG. 1 compares the results of the combing force measurements of the experiments carried out as described above at 1 min rinsing time with the inventive formulations F1b, F2b, F6b, and the control formulation C0b (control without test substance).

The results in FIG. 1 show that the inventive formulations F1b, F2b, F6b at 1 min rinsing time have a sharp reduction of the combing forces.

Example 4

Antistatic Finishing of Keratin Fibers

To test the antistatic behavior, the shadow silhouette method was used.

The pretreated hair tresses described above, a plastic comb, a spotlight and a projection field marked with concentric semicircles are used.

The experiments were carried out under standardized climatic conditions. The hair tress is hung up at a distance of 15 cm from the projection field. The spotlight is positioned at a distance of 145 cm from the hair tress so that a shadow falls on the projection field.

The hair tress is then combed five times in succession using the comb. The electrostatic charging is measured via the shadow silhouette by marking the two outer points of the shadow and determining the distance between them. The smaller the shadow area, the more effective the antistatic effect.

Result:

| Formulation (see Table 4) | Distance |
|---|---|
| C0b | 15 cm |
| F1b | 7 cm |
| F2b | 7.5 cm |
| F6b | 6.5 cm |
| F9b | 7 cm |
| V7b | 9 cm |
| V8b | 7.5 cm |
| V10b | 7.5 cm |
| V11b | 9 cm |

Example 5

Viscosities of the Example Formulations

Result:

| Formulation (see Table 1) | Brookfield viscosity (25° C.) (Sp. T-C, 30 rpm) |
|---|---|
| C0b | 5550 |
| F1a | 15000 |
| F2a | 30000 |
| F5a | 32000 |
| F6a | 23600 |
| F9a | 14000 |
| V7a | 11000 |
| V8a | 12000 |
| V10a | 10000 |
| V11a | 7000 |

The inventive formulations F1a, F2a, F5a, F6a and F9a exhibit significantly higher viscosities in comparison to the corresponding formulations based on the very well known emulsifiers VARISOFT® EQ F 75 and VARISOFT® BT 85.

Example 6

Long-Term Storage Stability

The formulations were stored at 40° C. for 3 months
Result:

| Formulation (see Table 1 and 1b) | Brookfield Viscosity 25° C. (Sp. T-C, 30 rpm) |
|---|---|
| C0b | Phase separation |
| F1a | 13000 |
| F2a | 25000 |
| F5a | 29000 |
| F6a | 20000 |
| F9a | 12000 |
| V7a | Phase separation |
| V10a | 5000 |
| V11a | 2000 |

After storage for three months at 40° C., the inventive formulations F1aL3, F2aL3, F5aL3, F6aL3 and F9aL3 exhibit significantly lower decreases in viscosity compared to the corresponding formulations based on the well known emulsifier VARISOFT® EQ F 75 and comparative examples V10aL3 and V11aL3. Shown here in particular is the positive effect of the exchange of a methyl group (V10aL3 and V11aL3) by a stearyl group on the nitrogen atom (F1aL3 and F9aL3).

a) 1 Min Rinsing Time After 3 Months' Storage at 40° C.

TABLE 6a

Results of the conditioning of hair at 1 min rinsing time after 3 months' storage at 40° C. After storage from 3 months at 40° C., the inventive formulations F1aL3, F2aL3, F5aL3, F6aL3 and F9aL3 exhibit hardly any modified conditioning performance (similar in stability as comparative example V8aL3 based on an alkyl quat), whereas the corresponding formulations based on comparative examples V10aL3 and V11aL3 have hardly any conditioning properties. Shown here in particular is the positive effect of the exchange of a methyl group (V10aL3 and V11aL3) by a stearyl group on the nitrogen atom (F1aL3 and F9aL3).

|  | Wet combability | Wet feel | Dry combability | Dry feel |
|---|---|---|---|---|
| Inventive formulation F1a | 4 | 4 | 4.5 | 5 |
| Inventive formulation F9a | 4 | 3.5 | 4 | 4.0 |
| Comparative formulation V8a (BT 85) | 4 | 4 | 4 | 4 |
| Comparative formulation V10a | 2 | 1.5 | 2 | 2 |
| Comparative formulation V11a | 1.5 | 2 | 2.5 | 2.5 |
| Control C0a (without storage) | 1.5 | 2 | 2 | 2 |

The invention claimed is:

1. A composition comprising
A) at least one hybrid quat of the general formula I)

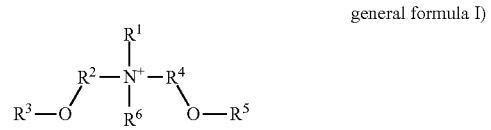

general formula I)

where
R$^1$ is a linear or branched mono alcohol having an alkyl group of 10 to 32 carbon atoms,
R$^2$ and R$^4$ are each independently identical or different, selected from the group of divalent hydrocarbon radicals having 1 to 4 carbon atoms,
R$^3$ is an acyl radical of a fatty acid having a chain length of 8 to 32 carbon atoms,
R$^5$ is H or an acyl radical of a fatty acid having a chain length of 8 to 32 carbon atoms,
R$^6$ is selected from the group consisting of hydrocarbon radicals having 1 to 4 carbon atoms,
B) at least one fatty alcohol.

2. The composition according to claim 1, wherein,
A) is present in an amount of from 0.1% by weight to 10% by weight, and
B) is present in an amount of from 1% by weight to 10% by weight, where the percentages by weight refer to the total composition.

3. The composition according to claim 1, wherein, in the at least one hybrid quat of the general formula I)
R$^1$ is a linear alkyl radical having 16 to 18 carbon atoms,
R$^2$ and R$^4$ are each independently, identical or different, selected from the group consisting of $C_2H_4$ and $C_3H_6$, $R^3$ is an acyl radical of a fatty acid having a chain length of 16 to 22, carbon atoms, $R^5$ is H or an acyl radical of a fatty acid having a chain length of 16 to 22, carbon atoms, $R^6$ is selected from the group consisting of ethyl and methyl.

4. The composition according to claim 1, wherein B) the at least one fatty alcohol is selected from the group consisting of octanol, decanol, lauryl alcohol, isolauryl alcohol, anteisolauryl alcohol, myristyl alcohol, isomyristyl alcohol, cetyl alcohol, palmoleyl alcohol, stearyl alcohol, isostearyl alcohol, anteisostearyl alcohol, eicosanol, petroselinyl alcohol, Guerbet alcohol, arachyl alcohol, gadoleyl alcohol, behenyl alcohol, erucyl alcohol, hectacosanol, octacosanol, and melissyl alcohol.

5. A hair conditioner comprising the at least one hybrid quat of the general formula I) according to claim 1.

6. A viscosity modifier comprising the at least one hybrid quat of the general formula I) according to claim 1.

7. The composition according to claim 1, wherein

A) is present in an amount of from 0.3% by weight to 5% by weight, and

B) is present in an amount of from 2% by weight to 8%, wherein the percentages by weight refer to the total composition.

8. The composition according to claim 1, wherein

A) is present in an amount of from 0.5% by weight to 3% by weight, and

B) is present in an amount of from 3% by weight to 6% by weight, wherein the percentages by weight refer to the total composition.

9. The composition according to claim 1, wherein $R^1$ is a hydrocarbon radical having 12 to 22 carbon atoms, $R^2$ and $R^4$ are each independently identical or different, selected from the group of divalent hydrocarbon radicals selected from the group consisting of $C_2H_4$ and $C_3H_6$, $R^3$ is an acyl radical of a fatty acid having a chain length of 12 to 22 carbon atoms, $R^5$ is H or an acyl radical of a fatty acid having a chain length of 12 to 22 carbon atoms, $R^6$ is selected from the group consisting of hydrocarbon radicals selected from the group of ethyl and methyl.

10. The composition according to claim 1, wherein $R^1$ is a hydrocarbon radical having 16 to 18 carbon atoms, $R^2$ and $R^4$ are each independently identical or different, selected from the group of divalent hydrocarbon radicals selected from the group consisting of $C_2H_4$ and $C_3H_6$, $R^3$ is an acyl radical of a fatty acid having a chain length of 16 to 22 carbon atoms, $R^5$ is H or an acyl radical of a fatty acid having a chain length of 16 to 18 carbon atoms, $R^6$ is selected from the group consisting of hydrocarbon radicals selected from the group of ethyl and methyl.

11. The composition according to claim 1, wherein $R^1$ is a hydrocarbon radical having 16 to 18 carbon atoms, $R^2$ and $R^4$ are each independently identical or different, selected from the group of divalent hydrocarbon radicals selected from the group consisting of $C_2H_4$ and $C_3H_6$, $R^3$ is an acyl radical of a fatty acid having a chain length of 16 to 18 carbon atoms, $R^5$ is H or an acyl radical of a fatty acid having a chain length of 16 to 22 carbon atoms, $R^6$ is selected from the group consisting of hydrocarbon radicals selected from the group of ethyl and methyl.

* * * * *